April 16, 1946. S. B. ROBERTS Plant Pat. 682
ROSE PLANT
Filed July 9, 1945
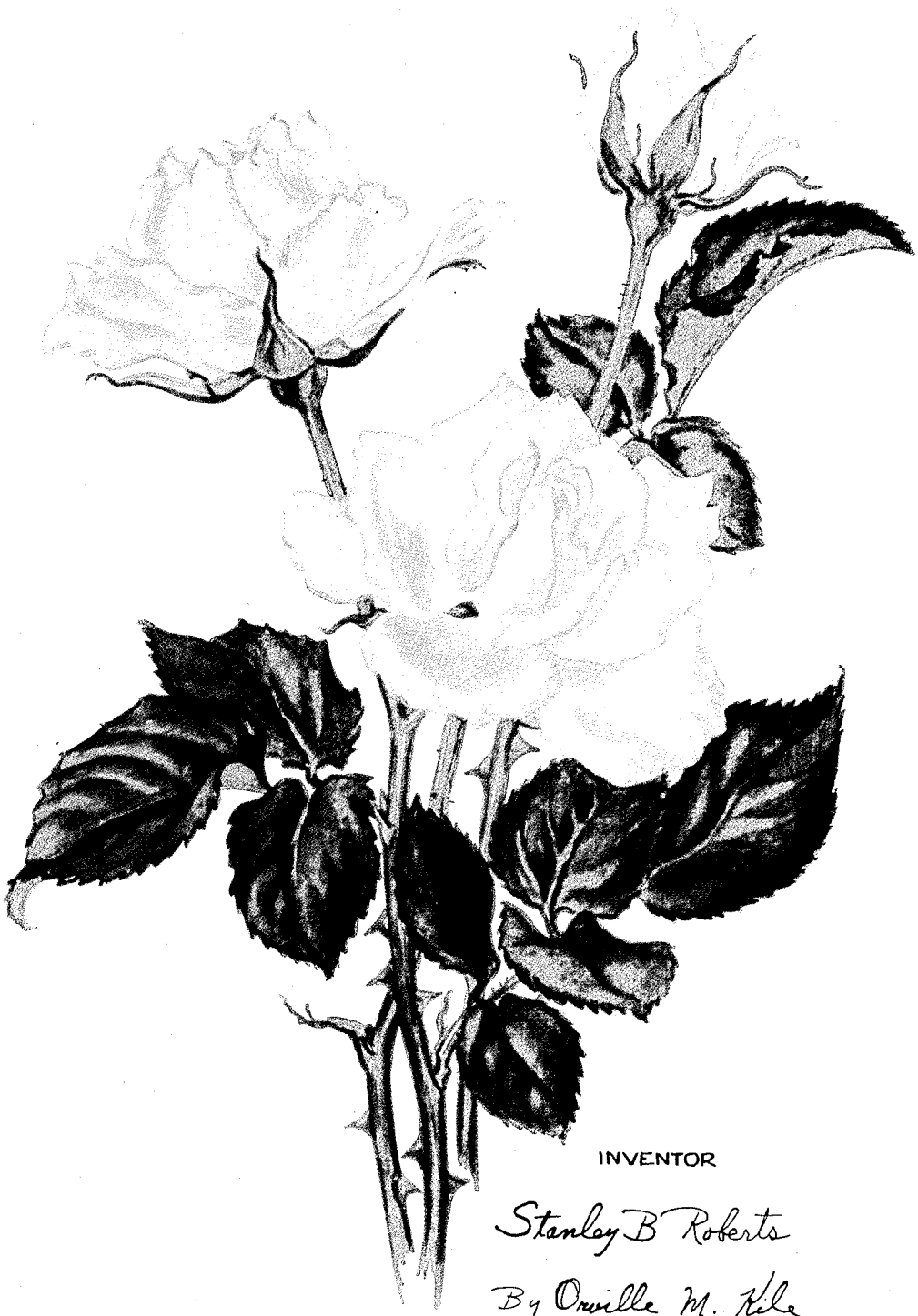
INVENTOR
Stanley B Roberts
By Orville M. Kile
PLANT PATENT AGENT Patented Apr. 16, 1946

Plant Pat. 682

UNITED STATES PATENT OFFICE

682

ROSE PLANT

Stanley B. Roberts, Madison, N. J.

Application July 9, 1945, Serial No. 603,946

1 Claim. (Cl. 47—61)

My present invention relates to a new and distinct variety of hybrid tea rose plant resulting from a cross made by me between an unknown variety and Queen Mary (Plant Patent 249). Its outstanding features are the distinctive, brilliant bi-color flower, vigorous growth and shining healthy foliage. Asexual reproduction through a number of years has proved these features to be firmly fixed.

Three specimens of the flower of my new variety are shown in the accompanying paintings in various stages of opening and in as nearly the true colors as the artist could paint them. However the color is elusive and varies somewhat in individual specimens.

Following is a detailed description of my new variety of rose. Color plate references indicate Ridgway's Color Standards and Nomenclature.

*The plant*

Growth: Vigorous and upright.

Foliage: Abundant; usually 3 to 5 leaflets.

*Size.*—Small; terminal leaflet averages 2 by 2½ inches, with lateral leaflets much smaller.

*Aspect.*—Soft; veins prominent; glossy.

*Rachis.*—Short; grooved.

*Stipules.*—Narrow; clinging except for long thin points.

*Shape.*—Oval with acuminate apex; edges sharply serrated.

*Color.*—Forest Green (Plate XVII).

Stems:

*Size and durability.*—Short; slender but strong.

*Color.*—Approximately Cress Green (Plate XXXI).

*Internodes.*—Short for hybrid tea roses.

*Thorns.* — Many; outward pointing; red tinged; with long, sharp points.

Disease resistance: Good.

*The flower*

Bud:

*Size.*—Medium, about 1½ to 2 inches long.

*Form.*—Long; pointed.

*Color.*—As calyx breaks, Apricot Yellow (Plate IV) blending into Light Cadmium (Plate IV) at base, with pinkish tinge at edge of petals.

Flower:

*Size.*—Medium, averaging 3½ to 4 inches in diameter.

*Form.*—Imbricated, with centers informal but covering stamens. Later opens into cupshape with outer petals somewhat quilled.

*Petalage.*—Double, having in November-December about 35 to 45 petals.

Petals:

*Size.*—Outer petals are 1½ to 1¾ inches in diameter each direction. Others smaller.

*Shape.*—Outer petals are almost round with some slight notching and undulation at edges; inner petals narrower.

*Texture and aspect.*—Substantial; soft and velvety to touch.

*Color.*—Bi-color. In most specimens the outer surface of petal is same as bud and the inner surface is Rose Doree (Plate I) about half way down, becoming coppery where this color blends with the large aiglet of Light Cadmium (Plate IV).

*Longevity.*—Excellent.

*Behavior.*—Clinging.

*Fragrance.*—Moderate.

Reproductive organs:

*Pistils.*—Many; bunched. Styles irregular lengths, mostly short. Approximately Eugenia Red (Plate XIII). Stigmas dull yellow.

*Stamens.*—Many, but fewer than pistils. Light Cadmium (Plate IV). Anthers large. Filaments short.

Having thus disclosed my invention, I claim:

The new and distinct variety of hybrid tea rose plant substantially as shown and described, characterized particularly by its vigorous growth, its abundant shiny foliage, and its distinctive bi-color flowers with outer surface of petals principally Apricot Yellow and inner surface principally Rose Doree.

STANLEY B. ROBERTS.